United States Patent
Hieber et al.

(10) Patent No.: US 8,596,274 B2
(45) Date of Patent: Dec. 3, 2013

(54) PATIENT INTERFACE SYSTEM

(75) Inventors: Robert Hieber, Export, PA (US);
William Kittridge, Pittsburgh, PA (US);
Eugene N. Scarberry, Trafford, PA (US); Thomas A. McCann, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 371 days.

(21) Appl. No.: 12/936,744

(22) PCT Filed: Apr. 7, 2009

(86) PCT No.: PCT/IB2009/051468
§ 371 (c)(1), (2), (4) Date: Oct. 7, 2010

(87) PCT Pub. No.: WO2009/125348
PCT Pub. Date: Oct. 15, 2009

(65) Prior Publication Data
US 2011/0023883 A1 Feb. 3, 2011

Related U.S. Application Data

(60) Provisional application No. 61/044,128, filed on Apr. 11, 2008.

(51) Int. Cl.
*A62B 18/08* (2006.01)
*A62B 18/02* (2006.01)
*A62B 18/00* (2006.01)
*A62B 17/04* (2006.01)
*A61B 16/00* (2006.01)

(52) U.S. Cl.
USPC ............ 128/207.11; 128/207.17; 128/206.21; 128/205.25; 128/201.23

(58) Field of Classification Search
USPC ............ 128/207.11, 206.24, 206.27, 206.21, 128/205.25, 206.28, 207.17, 201.25, 128/201.22, 207.21; 2/209, 425
See application file for complete search history.

(56) References Cited

U.S. PATENT DOCUMENTS 1,706,602 A * 3/1929 Drager et al. ............ 128/201.22
4,971,051 A 11/1990 Toffolon
(Continued)

OTHER PUBLICATIONS

Peter Chi Fai Ho, "Headgear Assembly", U.S. Appl. No. 11/849,675, filed Sep. 4, 2007.

*Primary Examiner* — Elizabeth Houston
*Assistant Examiner* — Ned T Heffner
(74) *Attorney, Agent, or Firm* — Michael W. Haas

(57) ABSTRACT

A patient interface system (30) that includes a patient interface assembly (40) and a headgear assembly (70). The patient interface assembly (40) includes a frame (42), a patient circuit connector (44), a seal member (46), and a coupling assembly (50) extending from the frame. The coupling assembly (50) is directed toward the users forehead when worn. The headgear assembly (70) includes an elongated pad support (72), a headgear attachment element (78) disposed on the pad support (72), a headgear strap (80) coupled to the headgear attachment element (78), and an elongated headgear pad (74) coupled to the pad support (72). The pad support, pad, or both are configured so as to extend from the forehead of the user generally along a centerline of the head and terminate proximate to a top of a head. In addition, a coupling assembly attachment assembly (100) is operatively coupled to the pad support (72) to couple the coupling assembly (50) of the patient interface device to the headgear assembly (70).

12 Claims, 17 Drawing Sheets

(56) References Cited

U.S. PATENT DOCUMENTS

| | | | |
|---|---|---|---|
| 5,012,533 A * | 5/1991 | Raffler | 2/420 |
| 5,438,981 A | 8/1995 | Starr | |
| 5,570,689 A * | 11/1996 | Starr et al. | 128/207.11 |
| 5,647,355 A | 7/1997 | Starr | |
| 5,647,357 A | 7/1997 | Barnett | |
| 5,662,101 A * | 9/1997 | Ogden et al. | 128/205.25 |
| 5,685,296 A | 11/1997 | Zdrojkowski | |
| 5,884,624 A | 3/1999 | Barnett | |
| 5,937,855 A | 8/1999 | Zdrojkowski | |
| 6,397,847 B1 | 6/2002 | Scarberry | |
| 6,584,977 B1 | 7/2003 | Serowski | |
| 6,851,425 B2 | 2/2005 | Jaffre | |
| 6,895,965 B2 | 5/2005 | Scarberry | |
| 7,066,179 B2 | 6/2006 | Eaton | |
| 7,069,932 B2 | 7/2006 | Eaton | |
| 7,237,551 B2 | 7/2007 | Ho | |
| 2003/0172936 A1 | 9/2003 | Wilkie | |
| 2006/0213521 A1 | 9/2006 | Radney | |
| 2006/0283460 A1 * | 12/2006 | Brown et al. | 128/206.24 |

* cited by examiner

PATIENT INTERFACE SYSTEM

CROSS REFERENCE TO RELATED APPLICATIONS

This application claims the benefit of International Application Number PCT/IB2009/051468, filed Apr. 7, 2009, and U.S. Provisional Application Ser. No. 61/044,128, filed Apr. 11, 2008.

The present invention pertains to patient interface system, and, in particular, to a patient interface system that includes a patient interface assembly that selectively attaches to a headgear assembly having an elongated headgear pad.

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient, to the airway of a patient/user. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, a variety of concerns must be taken into consideration. For example, in providing a pressure support therapy to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provides a tight enough seal against a patient's face without discomfort. A problem arises in that in order for the mask to maintain a seal without any undue gas leaks around the periphery of the mask, the mask cushion may be compressed against the patient's face.

Some conventional respiratory masks attempt to enhance mask stability by providing a relatively large structure that must be mounted on the patient's face. Therefore, an advantage exists for a respiratory mask that minimizes the amount of material that must be supported on the patient's head and face, yet provides a relatively high degree of stability, so that that the mask is not easily dislodged from the patient. Another advantage exists for a respiratory mask that evenly distributes the headgear strapping force needed to hold the mask on the patient at locations on the patient's face that are best suited to handle such forces.

Accordingly, it is an object of the present invention to provide a patient interface system that overcomes the shortcomings of conventional patient interface systems. This object is achieved according to one embodiment of the present invention by providing a patient interface system that includes a patient interface assembly and a headgear assembly. The patient interface assembly includes a frame, a patient circuit connector disposed on a first side of the fame, a seal member disposed on a second side of the frame opposite the first side and adapted to seal against a surface of a user, and a coupling assembly extending from the frame such that the coupling assembly is directed toward a forehead of a user responsive to the patient interface assembly being worn by such a user. The headgear assembly includes an elongated pad support, a headgear attachment element associated with the pad support, a headgear strap coupled to the headgear attachment element, and an elongated headgear pad is coupled to the pad support. The pad support, the pad, or both the pad support and the pad are configured so as to extend from a forehead region of a user generally along a centerline of such a user and terminate proximate to a top of a head of such a user responsive to the patient interface assembly being worn by such a user. The headgear assembly also includes a coupling assembly attachment assembly coupled to the pad support to couple the coupling assembly of the patient interface device to the headgear assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
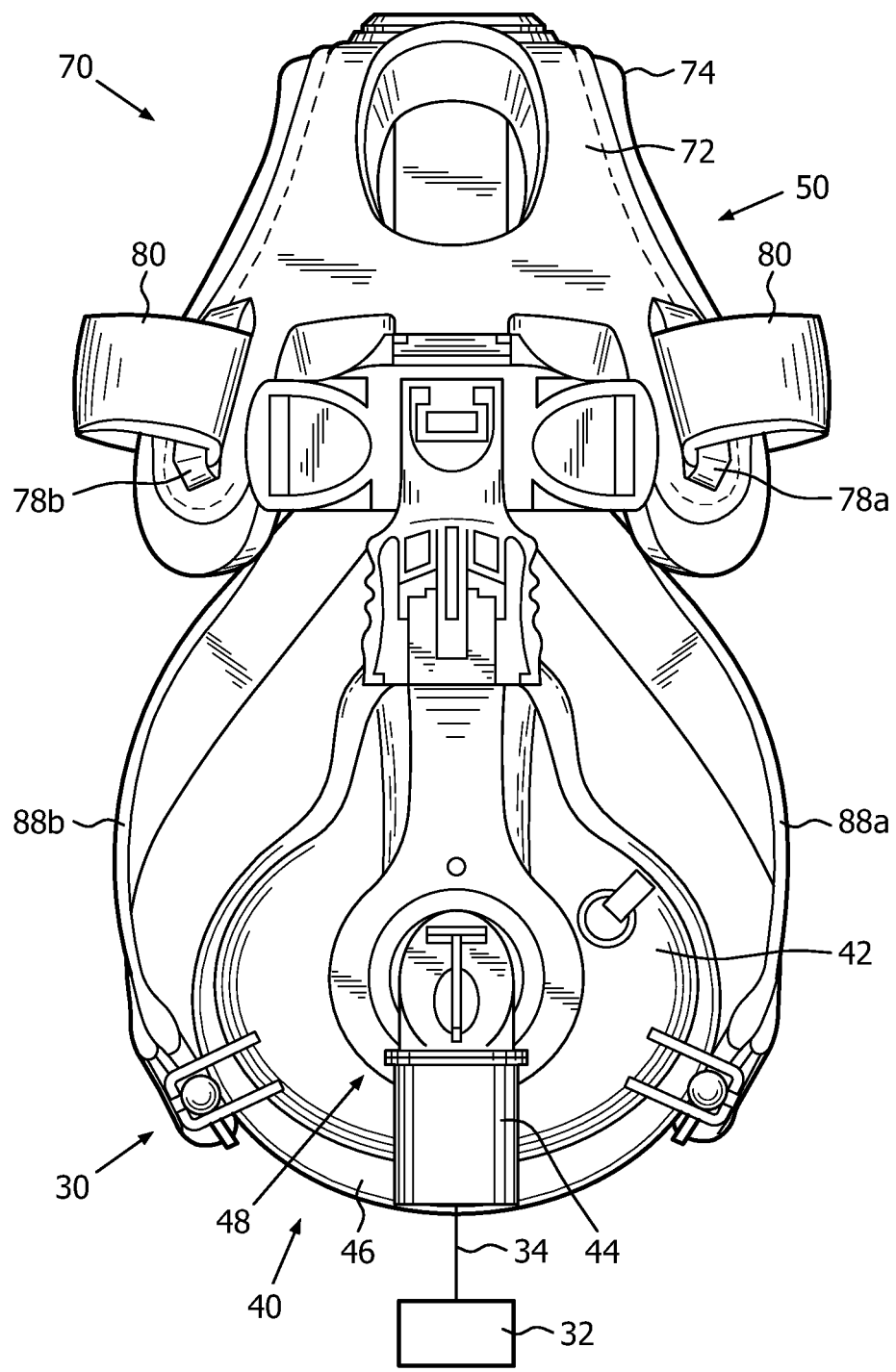
FIG. 1 is a front view of a first embodiment of patient interface system according to the principles of the present invention.
Figure 2:
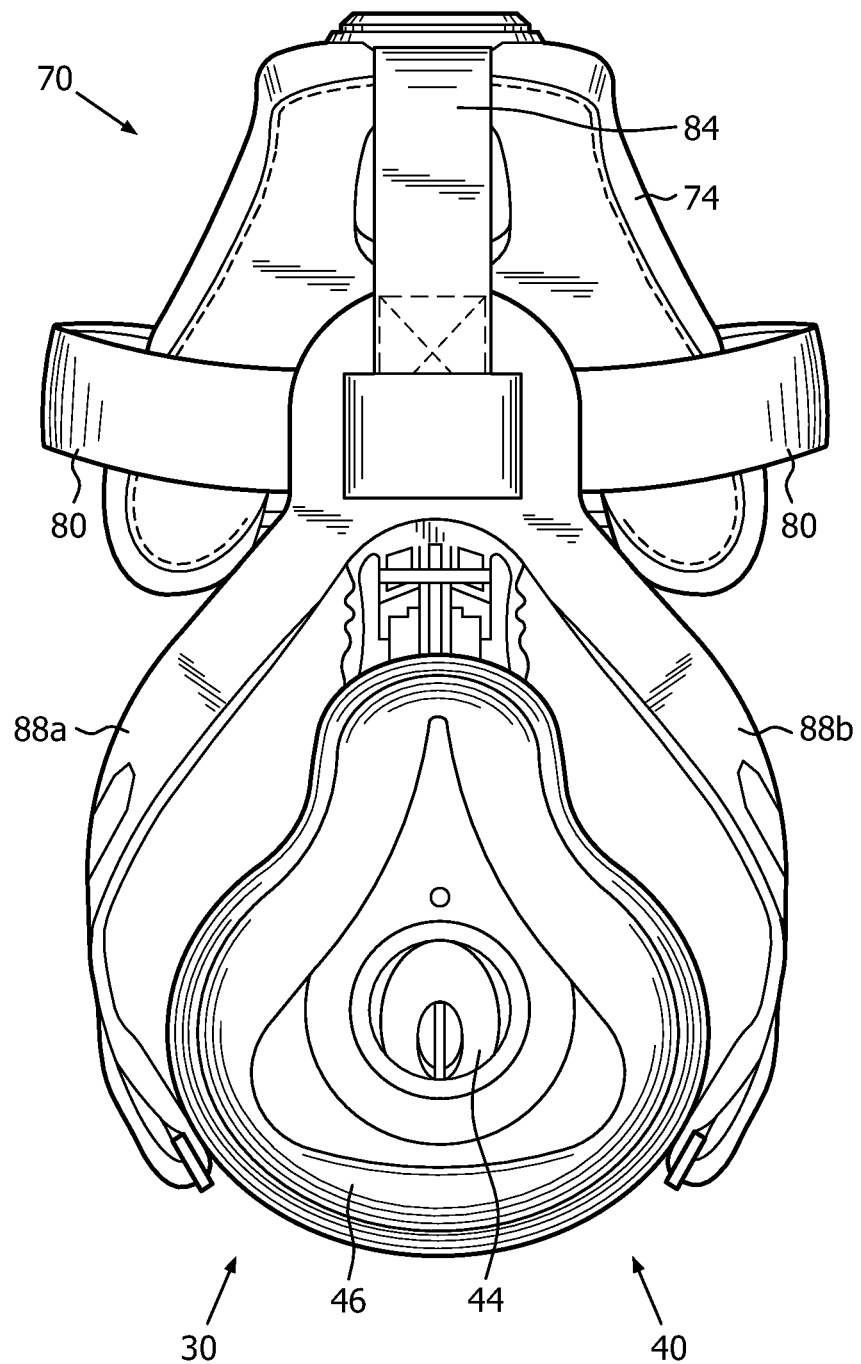
FIG. 2 is a rear view of the patient interface system of FIG. 1.
Figure 3:
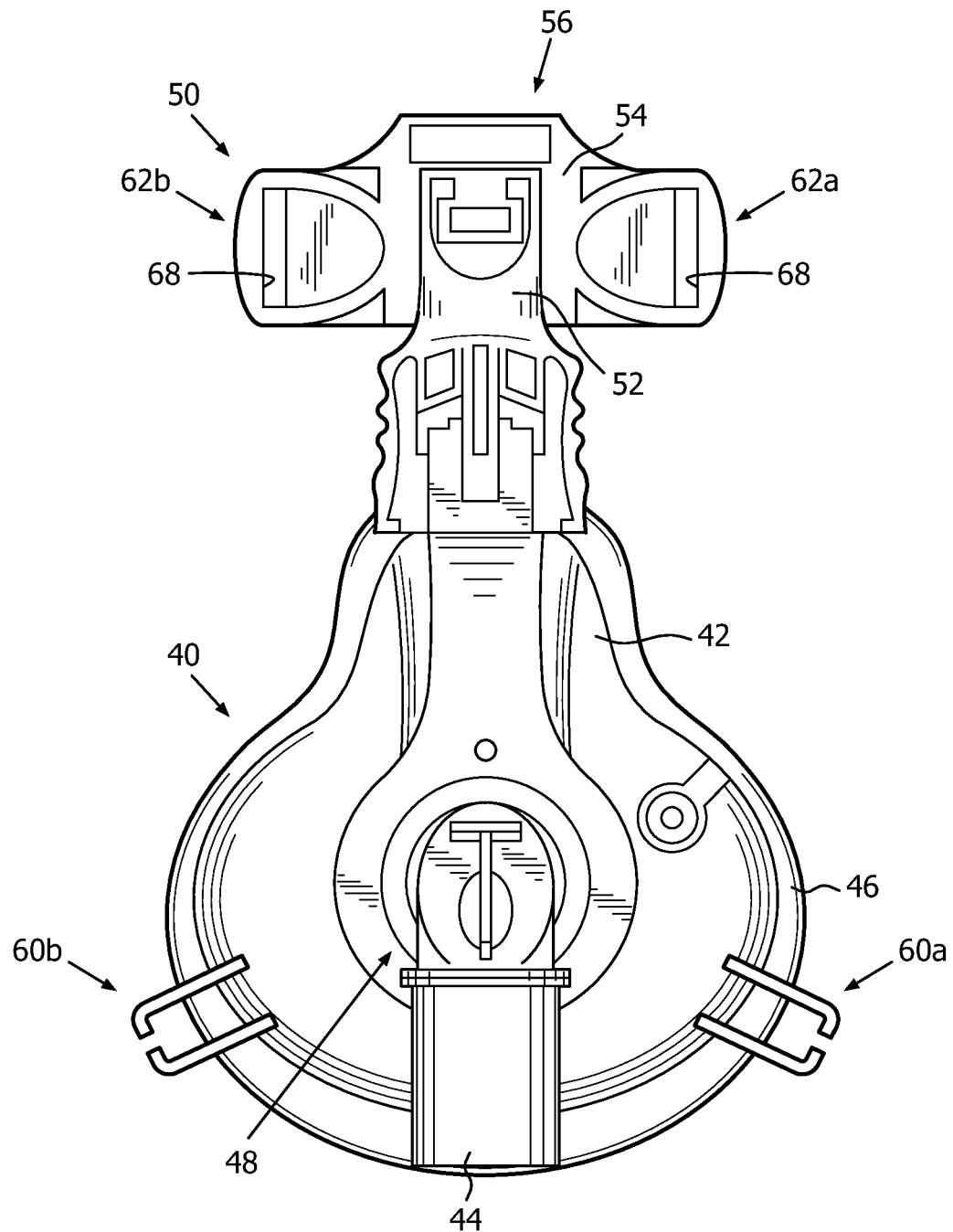
FIGS. 3 and 4 are front and rear views, respectively, of the patient interface assembly in the patient interface system of FIG. 1.
Figure 4:
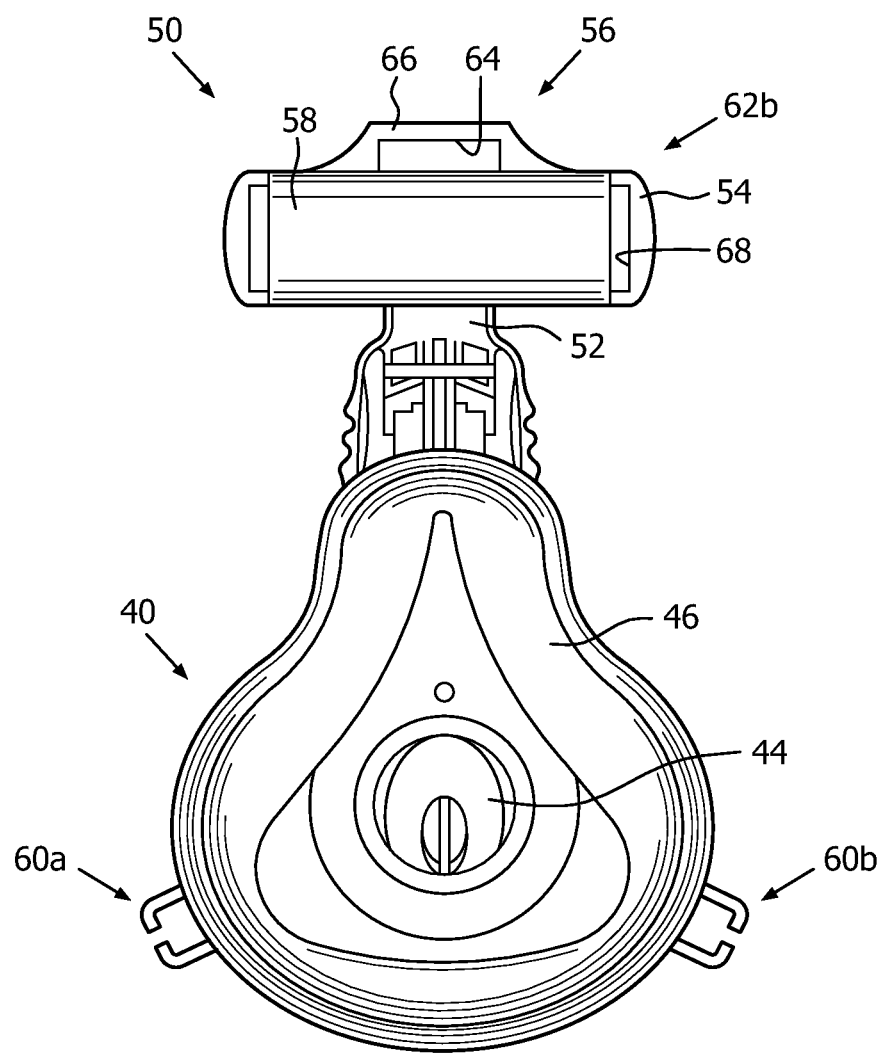
Figure 5:
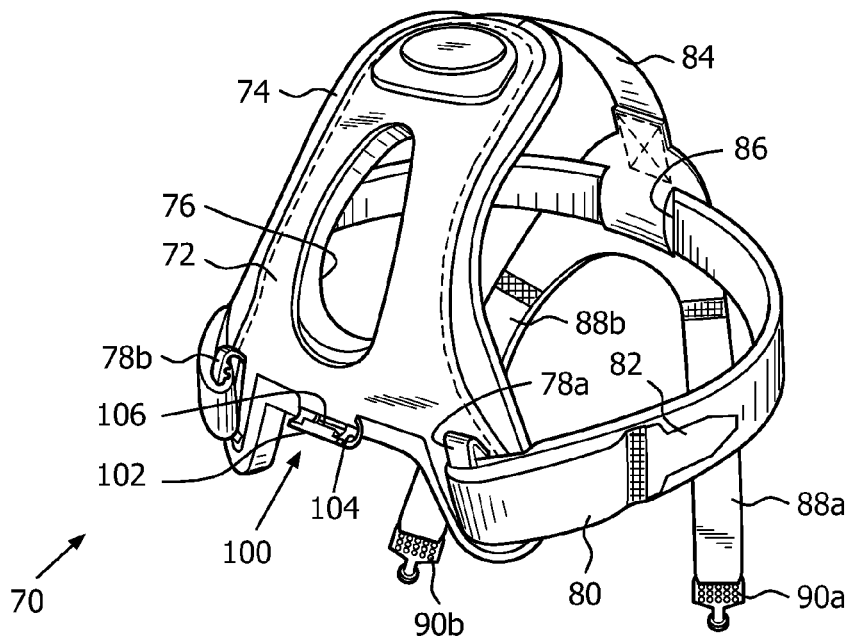
FIGS. 5 and 6 are front and rear perspective views, respectively, of the headgear assembly in the patient interface system of FIG. 1.
Figure 6:
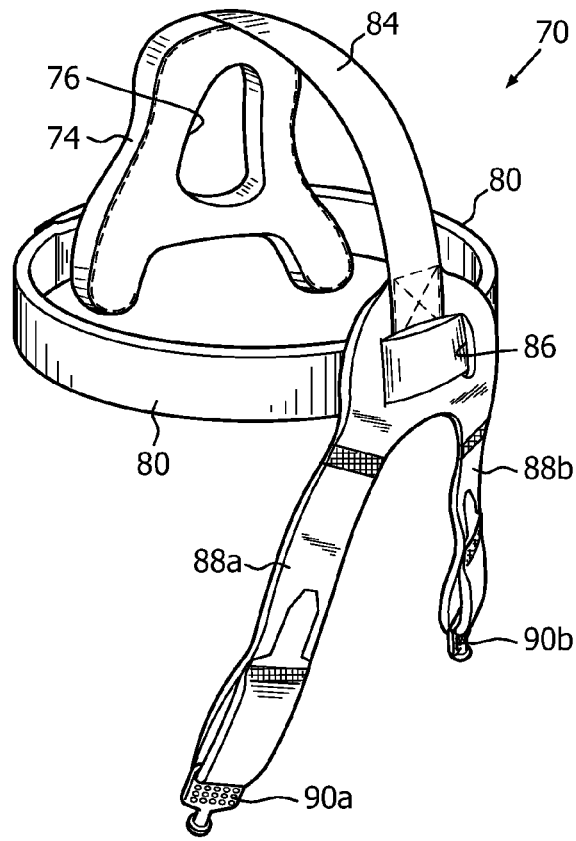

FIGS. 1-8 illustrate a first embodiment of a patient interface system 30 according to the principles of the present invention. Patient interface system 30 is shown schematically connected to a pressure support system 32 via a patient circuit 34, which communicates gas from the pressure support system to the patient interface system. Patient circuit 34 is any device, such as a flexible tubing, that carries the flow of gas from the pressure/flow generator in the pressure support system to the patient interface device.

As employed herein, the term "number" shall mean one or more than one and the singular form of "a", "an", and "the" include plural referents unless the context clearly indicates otherwise. Additionally as employed herein, the statement that two or more parts are "connected" or "coupled" together shall mean that the parts are joined together either directly or joined together through one or more intermediate parts, whereas the statement that two or more parts are "attached" or "affixed" shall mean that the parts are joined together directly.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Pressure support system 32 is any conventional ventilation or pressure support system. Examples of such pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance or loosening.

Patient circuit 34 can have any suitable configuration. For example, the patient circuit can be a single-limb tubing between the pressure support system and the patient interface system. Alternatively, the patient circuit can be a dual-limb tubing system; having an inspiratory limb for carrying a flow of gas to the user and a expiratory limb for carrying a flow of gas from the user. Typically, a Y-connector is provided near the patient that connects the inspiratory and expiratory limbs to the patient interface system.

It is to be further understood that various components may be provided in or coupled to pressure support system 32, patient circuit 34, patient interface system 30, or any combination thereof. For example, a bacteria filter, pressure control valve, flow control valve, pressure/flow/temperature/humidity sensor(s), meter, pressure filter, humidifier, and/or heater can be provided in or attached to the patient circuit.

Patient interface system 30 includes a patient interface assembly 40 and a headgear assembly 70. Patient interface assembly 40 overlies a portion of the face and communicates the flow of gas from the patient circuit to an airway of the user. Headgear assembly 70 serves to attach the patient interface assembly to the head of the user. It should be noted that the present invention also contemplates that patient interface assembly 40 can be used alone, as described in greater detail below. That is, the patient interface assembly can be coupled to the head of the user without using headgear assembly 70. Thus, the present invention provides the user with the flexibility to determine the specific configuration and/or technique for use in attaching the patient interface assembly to the user; with the headgear assembly, for example for improved stability, or without the headgear assembly, for example to minimize the amount of items provided on or otherwise coupled to the user's head.

Patient interface assembly 30 includes a frame 42, a patient circuit connector 44 disposed on a first side of the fame, and a seal member 46 disposed on a second side of the frame opposite the first side. The seal member, which is also referred to as a cushion, is adapted to seal against a surface of a user. In this illustrated exemplary embodiment, the frame and defines a nose receiving cavity for receiving the nose of the user and is formed from a relatively rigid material and supports the seal member.

Seal member 44 can be made from any suitable material, such as gel, silicone, foam, rubber, or combination of materials. Example of gel materials suitable for use as the seal member are described in U.S. Pat. Nos. 5,647,357; 5,884,624; 6,397,847; and 6,895,965 and pending U.S. patent application Ser. No. 11/715,760 (collectively referred to as "the gel references"), the contents of each of which are incorporated herein by reference. Seal member 44 can also be formed from a highly elastic material, such that that disclosed in U.S. patent application Ser. No. 11/266,808 (publication no. 2006-0096598), the contents of which are incorporated herein by reference.

The present invention further contemplates that seal member 44 may optionally include one or more flaps provided at a patient contacting portion of the cushion. An example of a cushion having multiple flaps is disclosed in U.S. Pat. No. 4,971,051, the contents of which are incorporated herein by reference. Furthermore, seal member 44 can include other structures, such as ribs, support members, varying wall thickness, and pleats to control the sealing characteristic of the cushion. An example of a cushion having pleats suitable for use in the present invention is disclosed in U.S. Pat. No. 7,237,551, the contents of which are incorporated herein by reference.

In an exemplary embodiment, patient circuit connector 44 is an elbow conduit coupled to an opening defined in fame 42 such that the patient circuit connector is rotatable relative to the frame. The present invention also contemplated providing an exhaust assembly, generally indicated at 48, in the patient circuit connector to allow gas, such as the patient's exhaled carbon dioxide, to exhaust to the ambient atmosphere. Exhaust assembly 48 can have any suitable configuration, such as one or more vent holes provided in the wall of patient circuit connector 44.

The present invention also contemplates that the exhaust assembly 48 can be configured to actively or passively control the amount of gas exhausting to atmosphere. For example, if the pressure in the patient circuit falls, the exhaust assembly can open to provide a large, direct access for the patient to ambient atmosphere. An example of such an exhaust assembly is disclosed in U.S. Pat. No. 6,851,425 the contents of which are incorporated herein by reference. Further examples of suitable exhaust assemblies for use with the present invention are disclosed in U.S. Pat. Nos. 5,438,981; 5,647,355; 5,685,296; 5,937,855; and 6,584,977, the contents of each of which are incorporated herein by reference. The present invention also contemplates providing the exhaust assembly in the mask shell, seal member, or any combination thereof. Finally, the assembly can also be omitted if exhausting gas from the system is not needed, which is typically the case in a dual-limb patient circuit configuration.

A coupling assembly, generally indicated at 50, extends from frame 42 such that the coupling assembly is directed toward a forehead of the user when the patient interface assembly is worn by the user. In the illustrated exemplary embodiment, coupling assembly 50 includes a support arm 52, a forehead arm 54 operatively coupled to the support arm, and a headgear coupling element, generally indicated at 56, coupled to the forehead arm. Support arm 52 can a adjustably coupled to frame 42 or fixed to the frame. Similarly, forehead arm 54 can be adjustably or selectively coupled to support arm 52. In an exemplary embodiment, support arm 52 is coupled to frame 42 such that the support arm slides over an arcuate path along the frame, as described, for example in the U.S. Pat. No. 7,069,932 ("the '932 patent"), the contents of which are incorporated herein by reference. In a further exemplary embodiment, forehead arm is rotatably coupled to support arm 52, as described in the '932 patent.

In this embodiment, coupling assembly 50 further includes a forehead pad 58 coupled to forehead arm 54. Pad 58 can be either fixed or removably coupled to the forehead arm. As can be appreciated from the description herein, forehead pad 58 is optional in many embodiments of the present invention. Forehead pad 58 can be form from any suitable material or combination of materials, such as gel, foam, silicon. Example of gel materials suitable for use as these pads are described in the gel references, the contents of each of which are incorporated herein by reference. Forehead pad 58 is shown as a unitary, single element. It to be understood that the present invention contemplates that forehead pad 58 can be defined by multiple pads coupled to the forehead arm.

The present invention contemplates that support arm 52, forehead arm 54, and forehead pad 58 can have any one of a variety of different configuration. For example, the forehead and support arms can be an integral, one-piece, assembly. In the illustrated embodiment, the support arm and the forehead arm have a generally "T" shape. As can be appreciated from reviewing further embodiments of the present invention, the present invention contemplates that these components can have a variety of other configurations. Also, the mechanism for adjustably coupling the support arm to the frame can have be any suitable connection. In the illustrated embodiment, the adjustment mechanism allows the support arm to be located in one of a plurality of discrete locations relative to the frame.

Headgear assembly 70 includes an elongated pad support 72 and an elongated headgear/forehead pad 74 coupled to the pad support. The pad support, the pad, or both the pad support and the pad are configured so as to extend from a forehead region of a user generally along a centerline of such a user and terminate proximate to a top of a head of such a user when the patient interface assembly is donned by the user. In the illustrated exemplary embodiment, pad support 72 and headgear pad 74 are generally elongated and curved along a radius of curvature (or having a curvature) that generally matches the front of the human head. This is perhaps best illustrated in FIGS. 7 and 8.

Pad support 72 is formed from a rigid or semi-rigid material, and headgear pad 74 is formed from a material suitable for contacting the surface of the user, such as foam. Pad support 72 and headgear pad 74 are coupled together in any suitable manner. In an exemplary embodiment, the pad support and headgear pad are sewn together. However, the present invention also contemplates selectively coupling the pad support and headgear pad, for examples using snaps or a hook-and-loop fastener, so that one can be removed from the other. This option, for example, allows the pad to be replaced as needed or allows for different sized pad support and headgear pads to be used with one another.

Pad support 72 and pad 74 are each shown as a unitary, single element. It to be understood that the present invention contemplates forming the pad support using multiple elements joined together. Likewise, pad 74 can be defined by a plurality of discrete pads. It is to be further understood that pad support and pad 74 can have a variety of sizes and configurations. For example, the pad and pad support shown in FIGS. 1-8 include an opening 76 generally in the middle of this structure. This opening allows air to flow to the user's head for increased comfort. This opening can be omitted or more than one such opening can be provided.

A plurality of headgear attachment elements 78a, 78b are associated with pad support 72. More specifically, headgear attachment elements 78a, 78b are provided on opposite sides at a first end of the pad support that is located proximate to the forehead of the user when the headgear assembly is on the user. In the illustrated embodiment, headgear attachment attachments 78a, 78b are formed by a protrusion extending from the pad support so that a slot is formed on the pad support.

A headgear strap 80 is coupled to headgear attachment elements 78a, 78b by being inserted through the slot defined by the headgear attachment attachments. In the illustrated embodiment, the headgear strap inserts through the headgear attachment attachments and wraps over upon itself. A fastening assembly 82 is provided at the end of the headgear strap to allow the user to control the effective length of the headgear strap by controlling the position where the free end of the strap attaches back onto the remaining portion of the headgear strap. The present invention contemplates that fastening assembly 82 can be any suitable fastener, such as a snap or buckle. In an exemplary embodiment, fastening assembly 82 is a hook-and-loop fastener, which is commonly known as a VELCRO® fastener.

A second headgear strap 84 is coupled to a second end portion of the pad support. The present invention contemplates that second headgear strap 84 is coupled to the pad support in any conventional manner and may be either fixed for selectively removable from the pad support. However, in an exemplary embodiment, the second headgear strap is fixed to the pad support, for example by being sewn to the pad support. Second headgear strap 84 extends from the end of pad support 72 along the centerline of the head from the front to the back of the head. First headgear strap 80 wraps around the head and is coupled to second headgear strap 84 at the back of the head. In an exemplary embodiment, second headgear strap 84 couples to first headgear strap 80 by passing first headgear strap 80 through one or more slots 86 defined in the second headgear strap. This enables the first headgear strap to move relative to the second headgear strap so that the headgear straps can be positioned on the patient properly.

Headgear assembly 70 includes third headgear straps 88a and 88b that extend from the junction of the first and second headgear straps from behind the user's head back toward the front (face) of the user. In this embodiment, the third headgear straps are fixed to the second headgear straps, for example, by sewing the third headgear straps to the second headgear straps. Of course, the third headgear straps can be separable from the second and first headgear straps.

A headgear clip 90a and 90b is coupled to each of the third headgear straps 88a and 88b. Headgear clip 90a and 90b are used to couple the headgear straps to patient interface assembly 40, and, in particular, to frame 42. In the exemplary embodiment, third headgear straps 88a and 88b are attached to headgear clips 90a and 90b by threading the third headgear straps through a slot provided in the headgear clip. The free end of the third headgear strap is then fastened back onto the third headgear strap using any conventional fastener, such as a snap or hook-and-loop fastener. This configuration allows the user to adjust the effective length of the third headgear straps.

Headgear clips 90a and 90b include a portion that engage a headgear clip coupling members 60a and 60b provided on patient interface assembly 40. In the illustrated exemplary embodiment, headgear clips 90a, 90b and headgear clip coupling members 60a, 60b are configured in a ball-an-socket configuration. An example of this configuration is disclosed in U.S. Pat. No. 7,066,179 ("the '179 patent") the contents of which are incorporated herein by reference. Of course, other configurations for the headgear clips and headgear clip coupling members are contemplated by the present invention. Indeed, other such configurations are disclosed in the '179 patent. Moreover, the present invention contemplates using any fastening technique for joining the headgear strap to the patient interface assembly including snaps, hooks, loops, clamps, or other connectors.

Patient interface assembly 40 includes second headgear attachment element 62a and 62b coupled to forehead arm 54. In the illustrated exemplary embodiment, headgear attachment elements 62a and 62b are provided on opposite ends of forehead arm 54, but other locations for these elements on the forehead arm and/or support arm 52 are contemplated by the present invention. Although the headgear attachment elements may take any one of a variety of configures, in a simple exemplary embodiment, the headgear attachment elements are defined by a slot 68 through with a headgear strap passes. As noted above with respect to headgear attachment elements 78a, 78b, the headgear strap inserts through the headgear attachment attachments and wraps over upon itself. A fastening assembly provided at the end of the headgear strap allows the free end of the strap to attach back onto the strap, allowing the user to control the effective length of the headgear strap.

Patient interface assembly 40 can be worn by the user and attached to the user's head without the need for headgear assembly 70. As a result, the patient interface system of the present invention is highly flexible and adapted to suit the particular needs of the patient, as well as the caregiver. When used without headgear assembly 70, patient interface assembly 40 can be attached to the user using any conventional four-point headgear. An example of a conventional headgear suitable for use in attaching just the patient interface assembly to the face of user is disclosed in U.S. patent application Ser. No. 11/849,675, the contents of which are incorporated herein by reference. The four-point headgear should be configured such that the headgear straps attach to headgear clip coupling members 60a, 60b, and to headgear attachment elements 62a and 62b. Of course, as noted above, headgear clip coupling members 60a, 60b and headgear attachment elements 62a and 62b can have other configurations, thereby facilitating the attachment of the patient interface assembly using any conventional headgear.

If the user desires to use patient interface assembly 40 with headgear assembly 70, the patient interface assembly is coupled to the headgear assembly and headgear attachment element 62a and 62b are not used as headgear strap attachment points. A coupling assembly attachment assembly, generally indicated at 100, is operatively coupled to pad support 72 and is adapted to couple to coupling assembly 50 of patient interface assembly 40, thereby joining patient interface assembly 40 with headgear assembly 70.

In an exemplary embodiment, coupling assembly 50 is adjustably coupled to coupling assembly attachment assembly 100 so that the patient interface assembly can be adjusted relative to the headgear assembly. However, the present invention also contemplates a non-adjustable connection, i.e., a connection in which there is only one position for patient interface assembly 40 relative to headgear assembly 70. In the embodiment shown in FIGS. 1-8, the connection between patient interface assembly 40 relative to headgear assembly 70 is a non-adjustable connection. In the embodiment shown in FIGS. 13, 15, 17, 20, and 22 the connection between patient interface assembly 40 relative to headgear assembly 70 is an adjustable connection, as described in more detail below.

Coupling assembly is coupled to headgear assembly 70 by the interaction of headgear coupling element 56 with coupling assembly attachment assembly 100. In the exemplary embodiment illustrated in FIGS. 1-8, headgear coupling element 56 includes a slot 64 and coupling assembly attachment assembly 100 includes a hook 102 adapted to be inserted into slot 64. Of course, the present invention also contemplates reversing this configuration so that the coupling assembly attachment assembly includes a slot and the headgear coupling element includes the hook for insertion into the slot.

In the illustrated exemplary embedment, headgear coupling element 56 and coupling assembly attachment assembly 100 are configured such that a bar member 66 formed by headgear coupling element 56 is disposed within a groove 104 defined in the crook of hook 102 when the patient interface assembly is coupled to the headgear assembly. The present invention contemplates providing a relatively small protrusion 106 on hook 102 to help maintain bar member 66 within groove 104.

Figure 7:
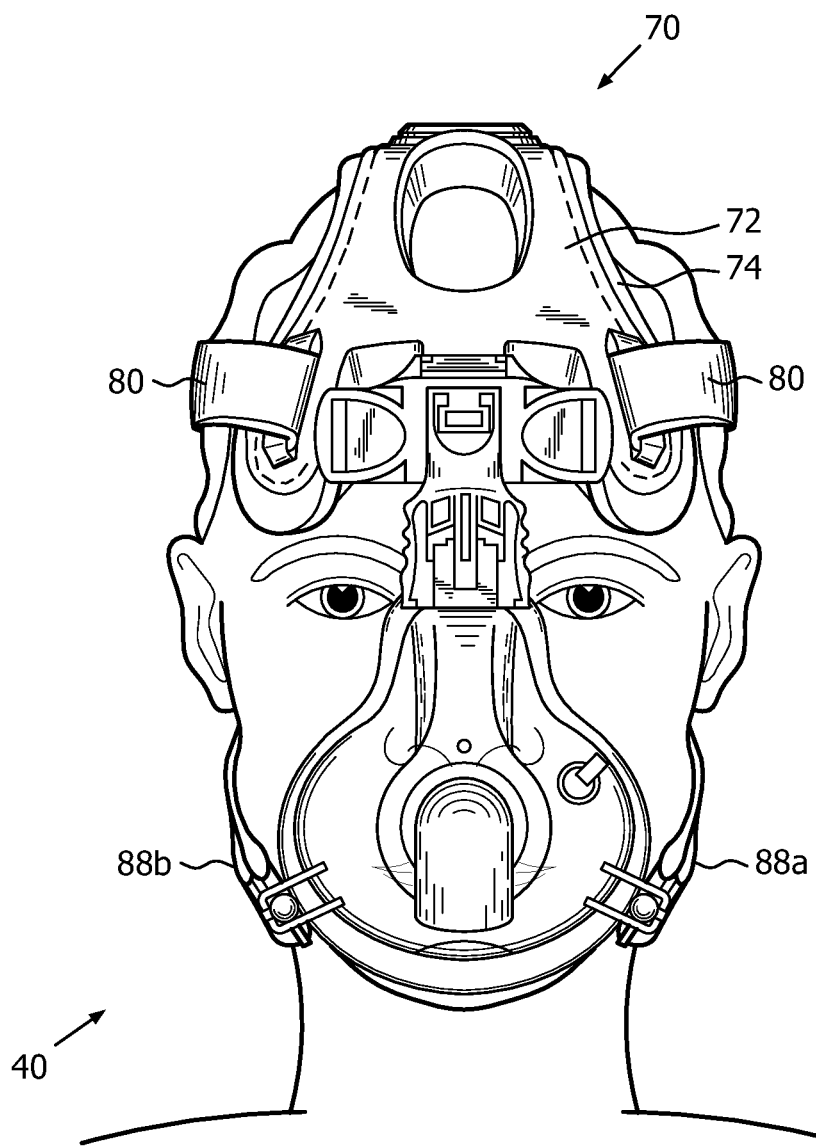
FIG. 7 is a front view of the patient interface system of FIG. 1 shown being worn by a user.
Figure 8:
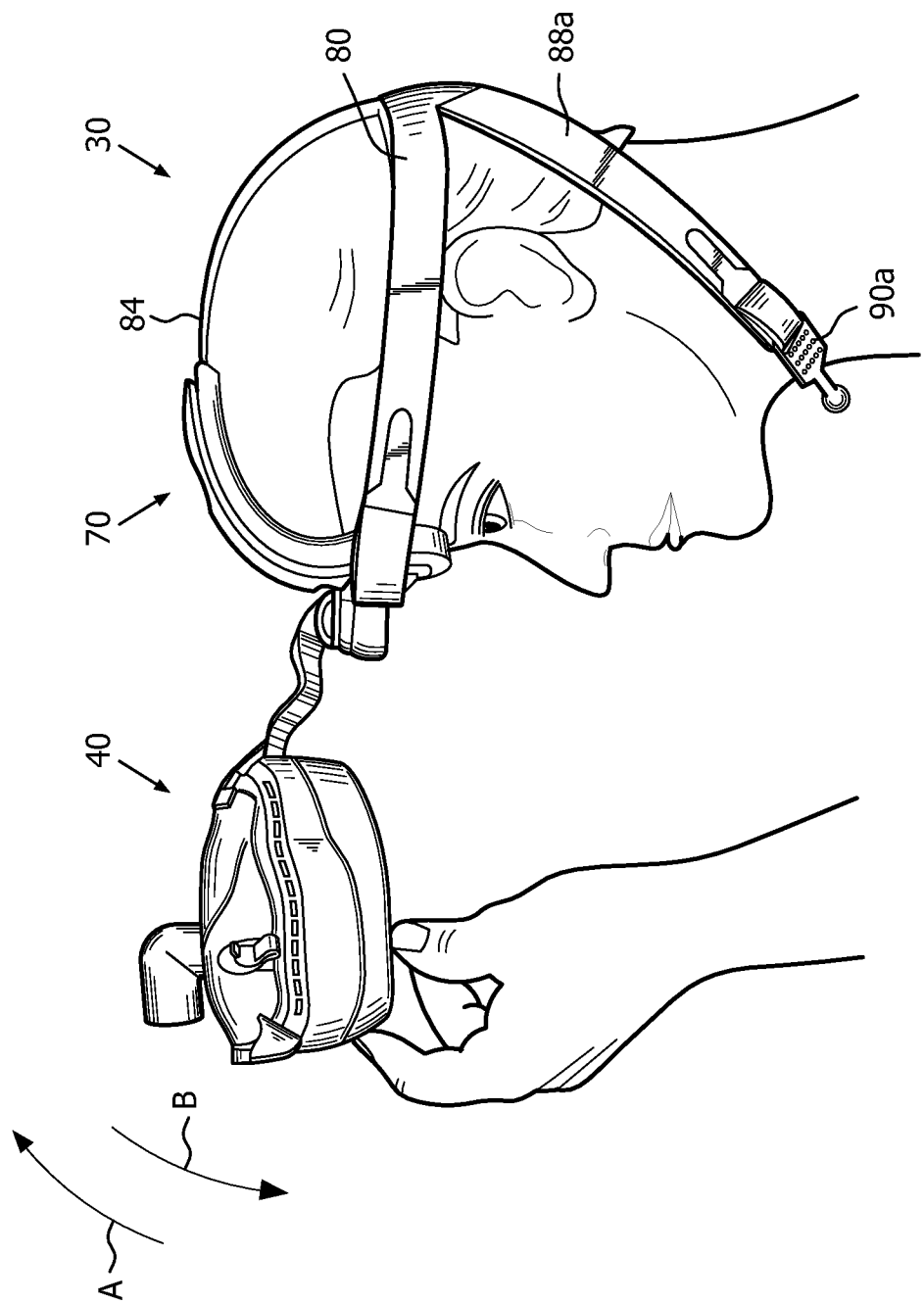
FIG. 8 is a side view of the patient interface system of FIG. 1 shown being attached or detached from the user.

In addition, headgear coupling element 56 and coupling assembly attachment assembly 100 are configured and oriented such that in the normal position shown in FIG. 7, coupling assembly 50 cannot be detached from headgear assembly 70, i.e., headgear coupling element 56 and coupling assembly attachment assembly 100 will not disengage. To disengage headgear coupling element 56 from coupling assembly attachment assembly 100, patient interface assembly 40, or at least coupling assembly 50, must be rotated or otherwise moved to an attaching/detaching position, such as that shown in FIG. 8. In the exemplary illustrated embodiment, this is accomplished by first detaching headgear clips 90a, 90b from headgear attachment elements 60a, 60b and pivoting the lower portion of patient interface assembly 40 away from the user toward the top of the head, as indicated by arrow A in FIG. 8. When in this position, bar member 66 can be removed from groove 104. The present invention contemplates that bar member 66 and/or groove 104 are shaped such that only when the patient interface assembly is rotated to the disengaging position, will the bar member be easily removable from the groove. Otherwise, it is very difficult to detach the two.

Attaching patient interface assembly 40 to headgear assembly 70 is accomplished by following the opposite procedure. Namely, the patient interface assembly is first placed into the attaching/detaching position, and the bar member is inserted into groove 104 by fully inserting hook 102 into slot 64. The patient interface assembly is then lowered down onto the face, as indicated by arrow B. Of course, the attaching and detaching steps can be accomplished without any portion of patient interface system 30 being worn by the user.

In the first exemplary embodiment illustrated in FIGS. 1-8, headgear assembly 70 and at least forehead arm 54 and forehead pad 58 of coupling assembly 50, are configured so that when the coupling assembly is joined to the headgear assembly, the combined structure provides a generally unitary forehead engaging structure. In other words, when headgear assembly 70 is joined to coupling assembly 50, the combined structures mate or other wise fit together so that the user is presented with a forehead/head pad that "feels" like a single large pad, rather than two or more discrete pads. This configuration is believed to provide a very stable platform for the patient interface assembly.

The generally close mating engagement between headgear assembly 70 and coupling assembly 50 is achieved in the embodiment illustrated in FIGS. 1-8 by providing a cutout 92 in pad support 72 and pad 74. Cutout 92 is configured and sized to generally match the size and shape of forehead arm 54, so that the forehead fits snugly into the headgear assembly. Forehead pad 58 and pad 74 are sized and configured so that the surface that contacts the user defined by these pads is generally uniform, i.e., has a uniform height. Pads 58 and 74 can be formed from the same material to enhance the single pad feel of the combined assembly.

As noted above, the present invention also provides the flexibility for the user to employ only the patient interface assembly using headgear attachments points 60a, 60b, 62a, and 62a to couple to a conventional headgear. If desired, the user can add headgear assembly 70.

Figure 9:
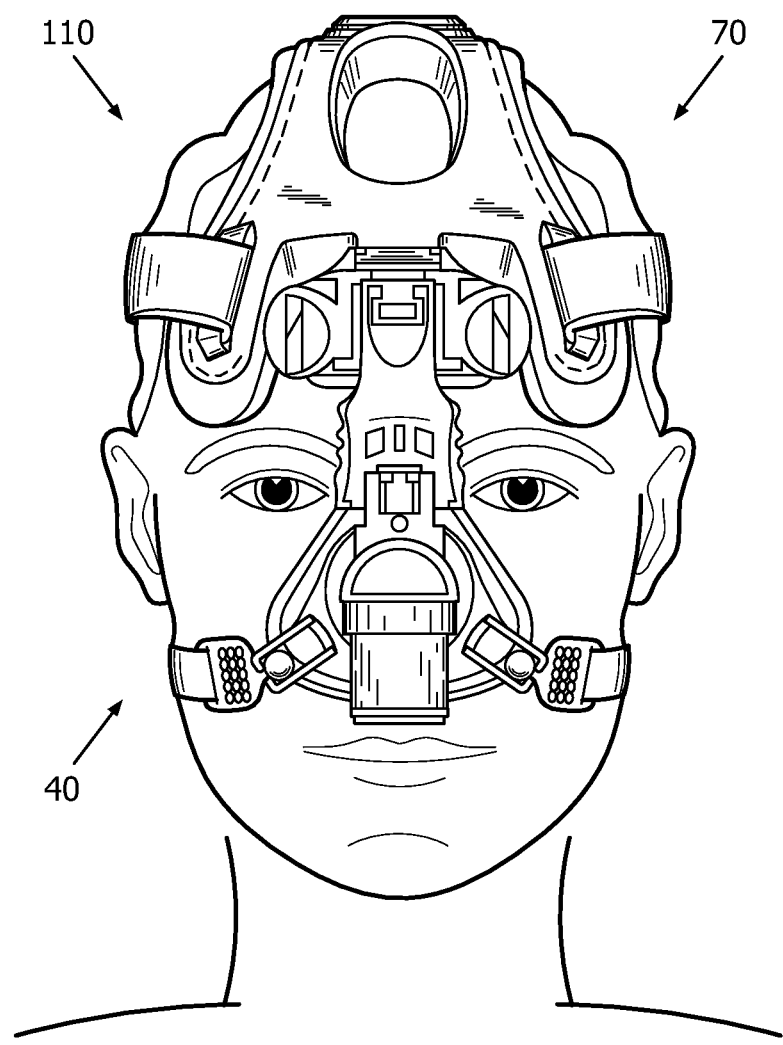
FIG. 9 is a front view of the second embodiment of patient interface system according to the principles of the present invention shown being worn by a user.
Figure 10:
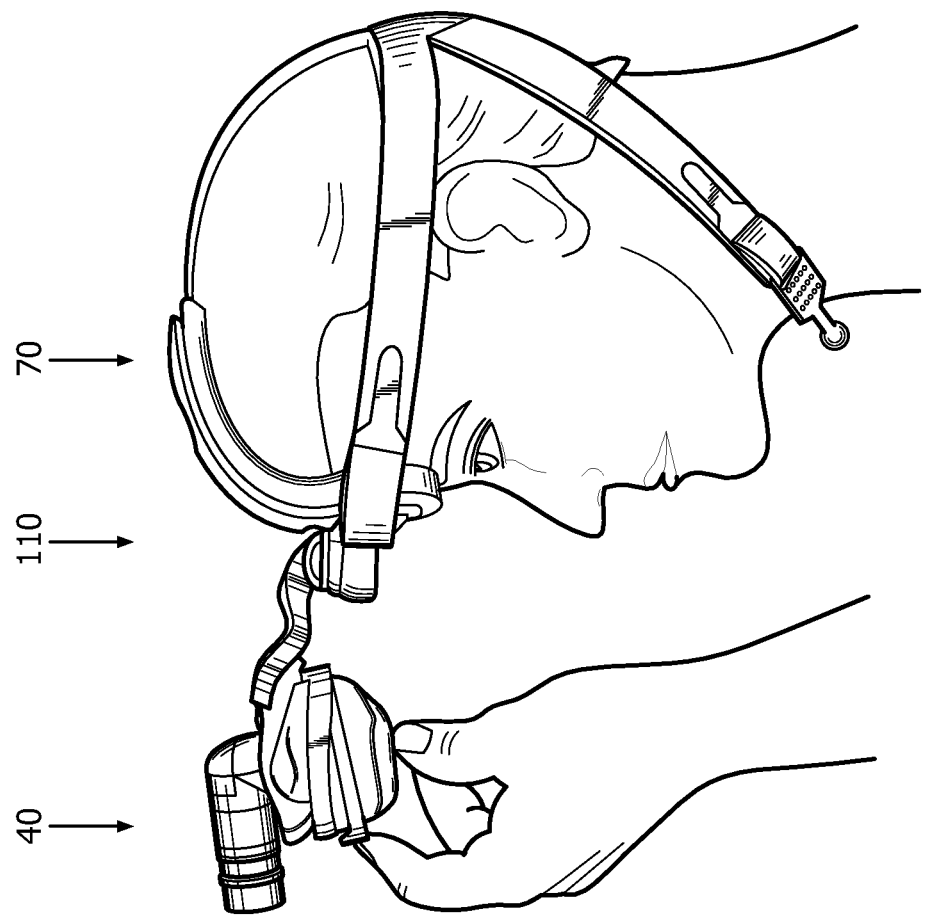
FIG. 10 is a side view of the patient interface system of FIG. 9 shown being attached or detached from the user.

In the illustrated embodiment, patient interface assembly 40 is a full face mask that seals over the user's nose and mouth. It is to be understood that the present invention contemplated that the patient interface assembly can have any suitable configuration. For example, FIGS. 9 and 10 illustrate a second embodiment of a patient interface system 110 in which patient interface assembly 112 is a nasal mask that seals only over the nose of the user. Patient interface assembly 112 coupled to headgear 70 in the same manner discussed above.

As noted above, the present invention contemplates a myriad of different configurations for attaching the patient interface assembly to the headgear assembly. The remaining figures, i.e., FIGS. 11-22, illustrate some of these possible configurations. For the sake of brevity, many of the features of the patient interface system are not reproduced in each of these figures so that the focus is on the item of interest.

Figure 11:
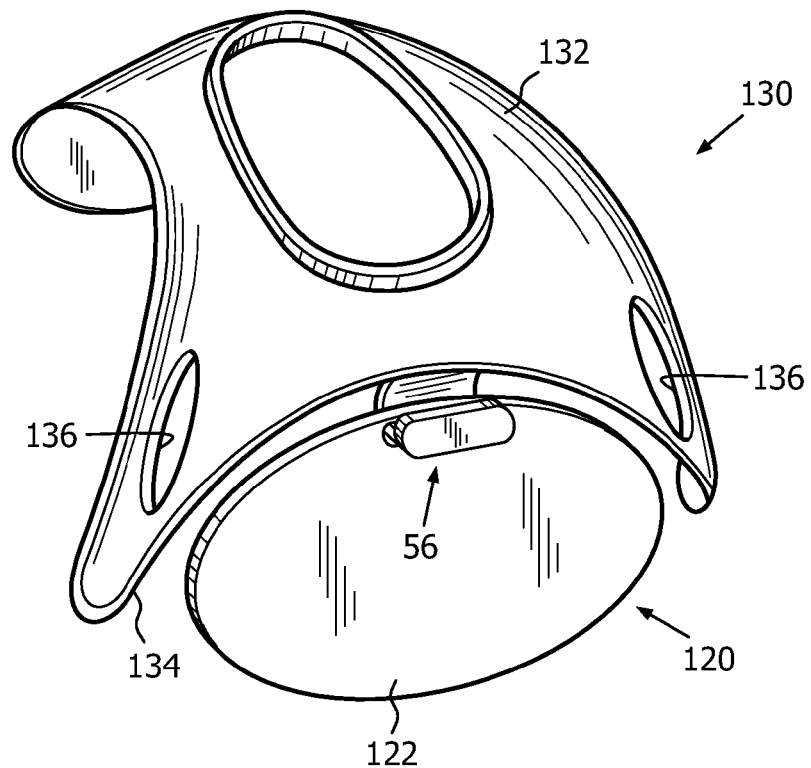
FIG. 11 is a perspective view of a third embodiment of a portion of a patient interface system according to the principles of the present invention.
Figure 12:
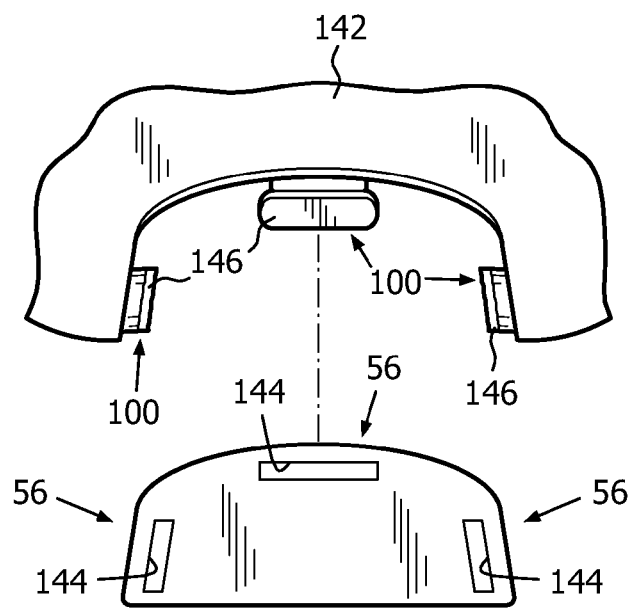
FIG. 12 is a front view of a fourth embodiment of a portion of a patient interface system according to the principles of the present invention.

FIG. 11 illustrates third embodiment of a portion of a patient interface system that includes a coupling assembly 120, more specifically, a forehead arm 122 adapted to coupled to headgear assembly 130. In this embodiment, headgear coupling element 56 and coupling assembly attachment assembly 100 have the same hook and slot configuration discussed above and are used to couple forehead arm 122 to a pad support 132. In this embodiment, however, forehead arm 122 and pad support 132 (and also the forehead pad) have a different configuration from that shown in FIGS. 1-8. In this embodiment, forehead arm 122 is generally oval, and pad support 132 has a curved end surface 134 that generally matches the curved shape of the forehead arm.

This embodiment serves to illustrate further alternative configurations for the coupling assembly and headgear assembly that are contemplated by the present invention. Also, headgear attachment elements 136 are slits or slots defined in the pad support, rather than being a raised protrusion as in the previous embodiment.

In the previous embodiment, the forehead arm had a single headgear coupling element. In the embodiment illustrated in FIG. 12, forehead arm 140 includes a plurality of headgear coupling elements 56. In this embodiment, headgear coupling elements 56 are again slots 144 defined in the forehead arm. Forehead pad support 142 includes a plurality of corresponding coupling assembly attachment assemblies 100. In this embodiment, coupling assembly attachment assemblies 100 are again hooks or protrusions 146 extending from pad support 142 that insert or snap into slots 144.

Figure 13:
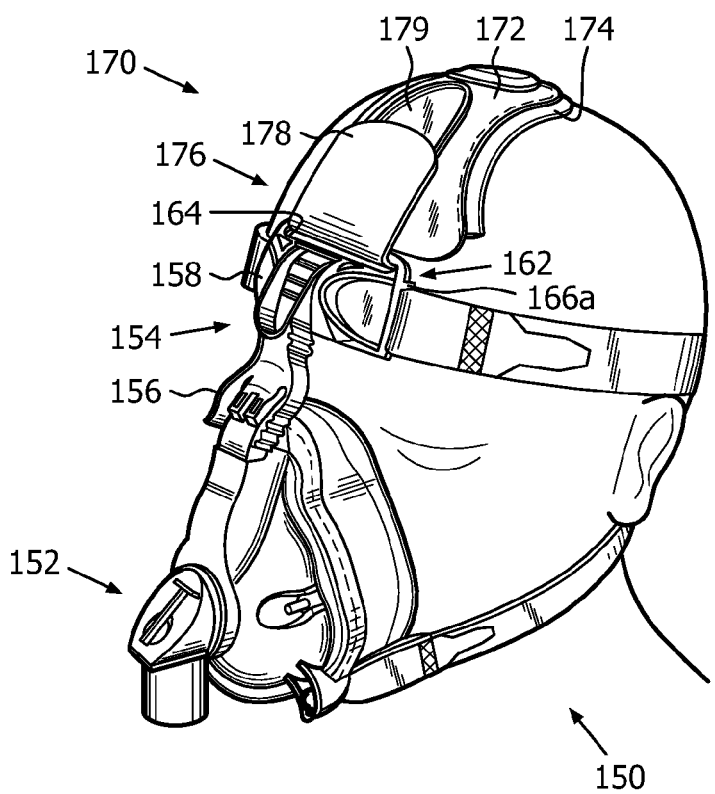
FIG. 13 is a perspective view of a fifth embodiment of a patient interface system according to the principles of the present invention shown being worn by a user.
Figure 14:
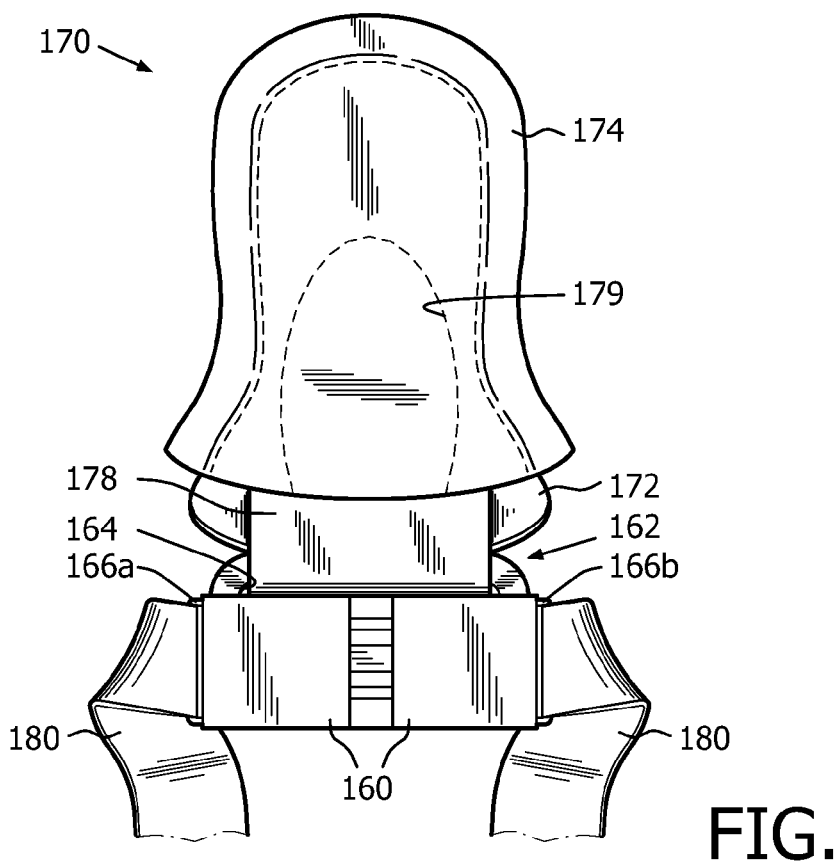
FIG. 14 is a rear view of a portion of the headgear assembly shown in FIG. 13.

FIGS. 13 and 14 illustrates fifth embodiment of a patient interface system 150 according to the principles of the present invention shown being worn by a user. As in the previous embodiments, patient interface system 150 includes a patient interface assembly 152 and headgear assembly 170, however, they are coupled together is a slightly different fashion. In this embodiment, patient interface assembly 152 includes a coupling assembly 154 having a support arm 156 and a forehead arm 158, with a pair of forehead pads 160 coupled to the forehead arm. A headgear coupling element 162 is provided at the end of forehead arm 158. In this embodiment, the headgear coupling element is a relatively long slot 164 defined near the upper edge of the forehead arm. Headgear attachment elements 166a and 166b are provided at each end of the forehead arm.

Headgear assembly 170 includes a forehead pad support 172 and forehead pad 174 coupled to the pad support. Pad support 172, however, does not include headgear attachments elements (78a, 78b in FIG. 1). Instead, headgear straps 180 are coupled to headgear attachment elements 166a and 166b on forehead arm 158. Headgear assembly 170 also includes a coupling assembly attachment assembly 176 coupled to forehead pad support 172 to attached to headgear coupling element 162 on forehead arm 158. Rather than a rigid hook, a coupling assembly attachment assembly 176 is a flexible strap 178.

In this embodiment, patient interface assembly 152 couples to headgear assembly 170 by inserting strap 178 into slot 164. The free end of strap 178 is then secured to pad support 172 using any conventional technique. In the illustrated embodiment, a hook-and-loop type of fastener is used, with one portion, e.g., the hook, being provided on strap 178 and another portion, e.g., the loop material, being provided on the pad support. In the illustrated exemplary embodiment, a portion of the hook-and-loop faster is disposed in opening 179 provided in pad support 172. This configuration allows the user to adjust how closely the forehead arm is to the pad support. While a single strap 178 is shown for use in coupling assembly attachment assembly 176, it is to be understood that multiple straps and associated slots in the forehead arm are contemplated by the present invention.

Figure 15:
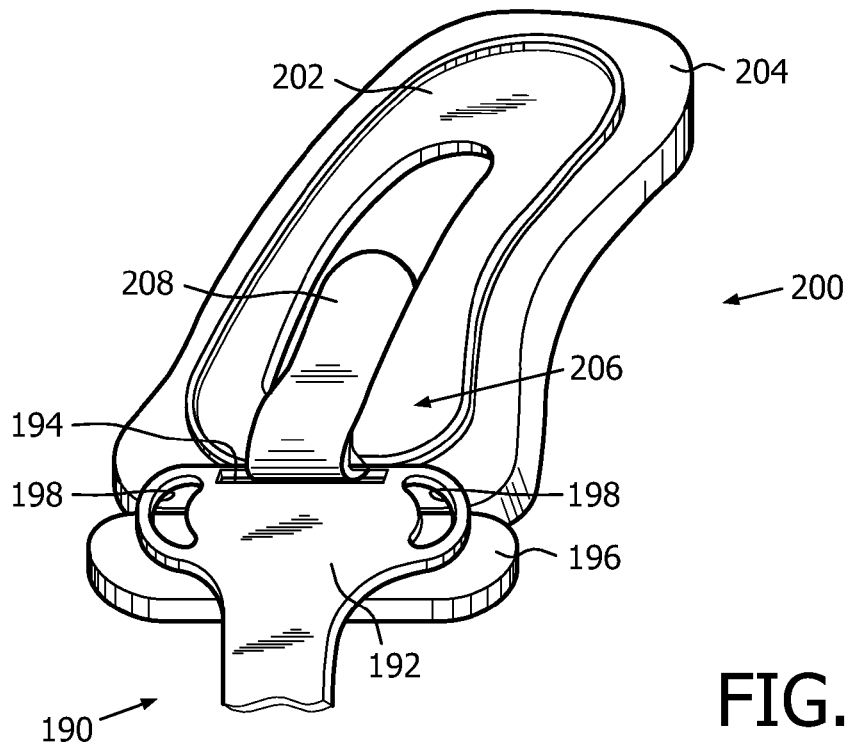
FIG. 15 is a front perspective view of a portion of a patient interface system according to a sixth embodiment of the present invention.

FIG. 15 is a front perspective view of a portion of a patient interface system according to a sixth embodiment of the present invention. More specifically, this embodiment illustrates a coupling assembly 190 portion of a patient interface assembly coupled to a headgear assembly 200. Coupling assembly 190 that includes an integral support and forehead arm 192 having a headgear coupling element 194 and headgear attachment elements 196. In this embodiment, headgear coupling element 194 and headgear attachment elements are slots. A forehead pad 198 is also coupled to arm 192.

Headgear assembly 200 includes a pad support 202 and pad 204 coupled to the pad support. Headgear assembly 200 includes a coupling assembly attachment assembly 206 coupled to pad support 202 to attached to headgear coupling element 194 on arm 192. As in the immediately prior embodiment, coupling assembly attachment assembly 206 is a flexible strap 208. The flexible strap inserts through the slot defining headgear coupling element 194 and is secured to pad support 202, pad 204, or another structure coupled to the pad or pad support.

In this embodiment, forehead pad 198 is slightly offset from arm 192 so that a portion of arm 192 and/or headgear coupling element 194 overlies pad 204 when the patient interface assembly is coupled to the headgear assembly. This serves to provide stability to the patient interface assembly. Forehead pad 190 and pad 204 are configured for mating engagement, i.e., the abutting edges are similarly contoured so that they fit closely together.

Figure 16:
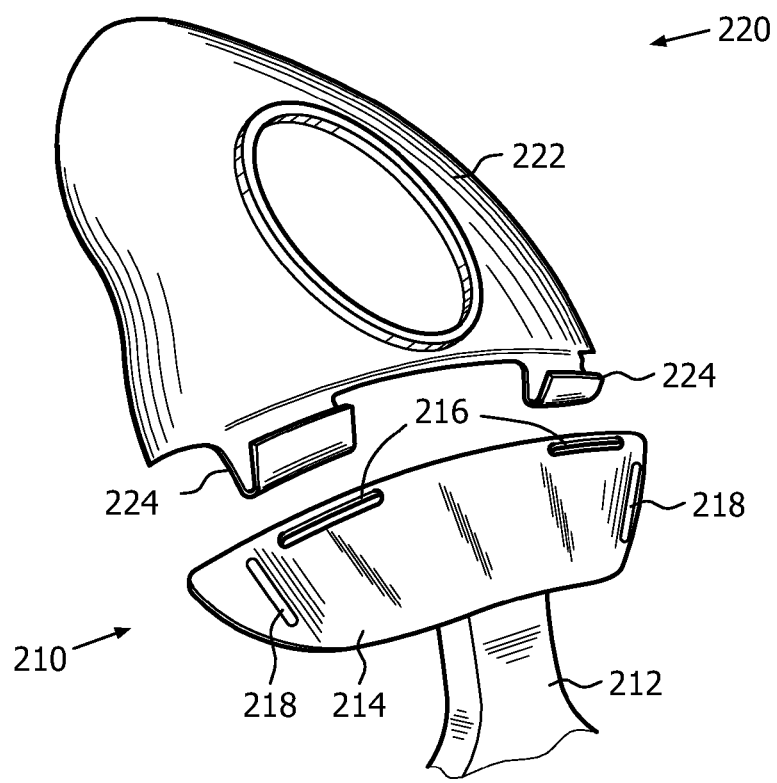
FIG. 16 is a front perspective view of a portion of a patient interface system according to a seventh embodiment of the present invention.

FIG. 16 is a front perspective view of a portion of a patient interface system according to a seventh embodiment of the present invention. This embodiment shows a coupling assembly 210 portion of a patient interface assembly and a corresponding headgear assembly 220. Coupling assembly 210 includes a support arm 212 and a forehead arm 214. The forehead arm includes a headgear coupling element 216 in the form of a pair of slots defined in the upper portion of the forehead arm, and headgear attachment elements 218 in the form of slots provided on each end of the forehead arm.

Headgear assembly include a pad support 222 and a coupling assembly attachment assembly 224 coupled to pad support 222. In this embodiment, there are no headgear attaching elements associated with the portion of the pad support near coupling assembly attachment assembly 224. Coupling assembly attachment assembly 224 includes a hook or protrusion extending from the pad support. The hooks engage the associated slots in the forehead arm to attached the headgear assembly to the patient interface assembly. Although not shown, a pad is coupled to pad support 222, and a forehead pad can be coupled to forehead arm 214. Alternatively, no pad need be coupled to forehead arm 214. The pad under pad support 222 can be extended to underlie all or part of the forehead arm when the forehead arm is coupled to the pad support.

Figure 17:
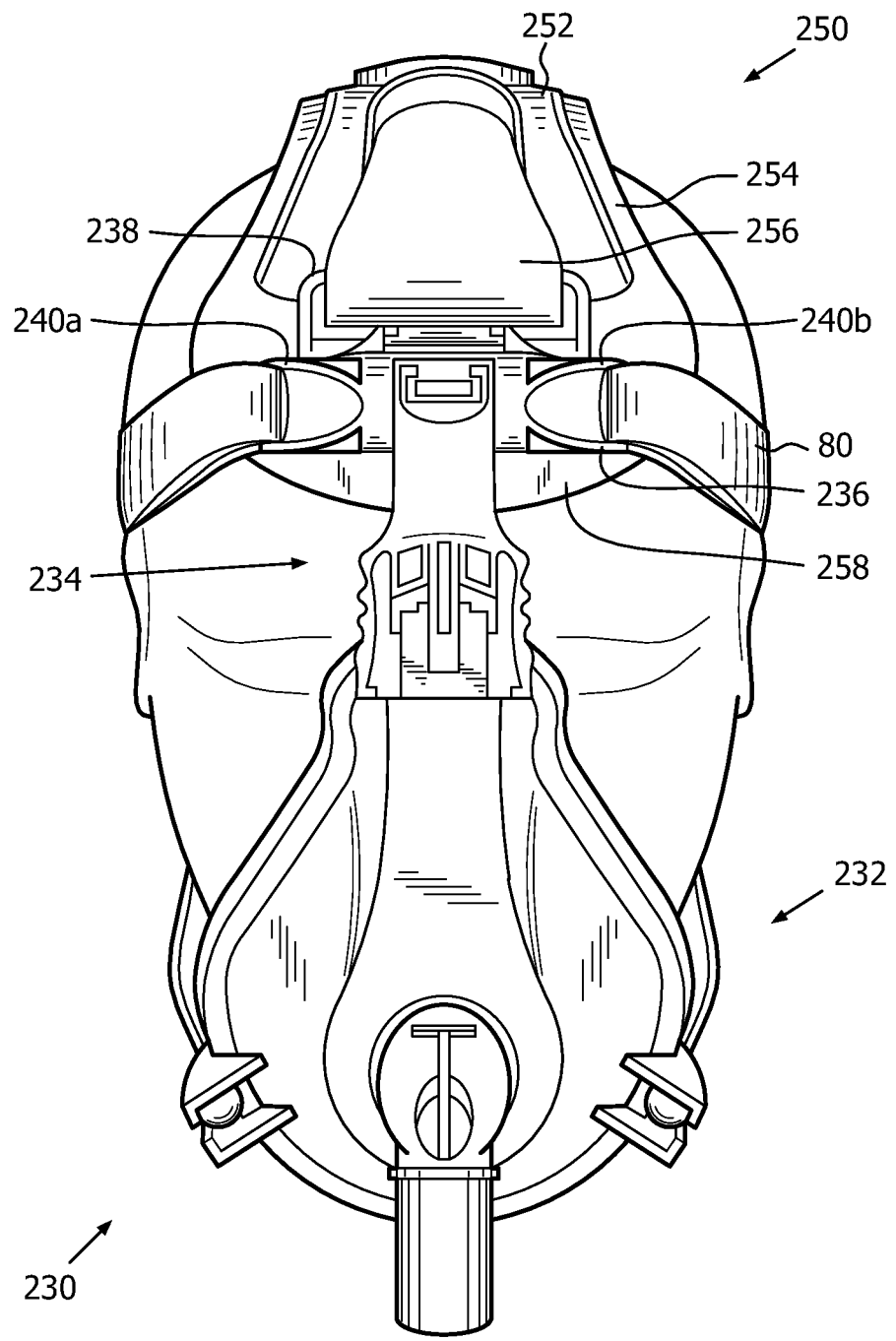
FIG. 17 is a front view of an eighth embodiment of a patient interface system according to the principles of the present invention shown being worn by a user.
Figure 18:
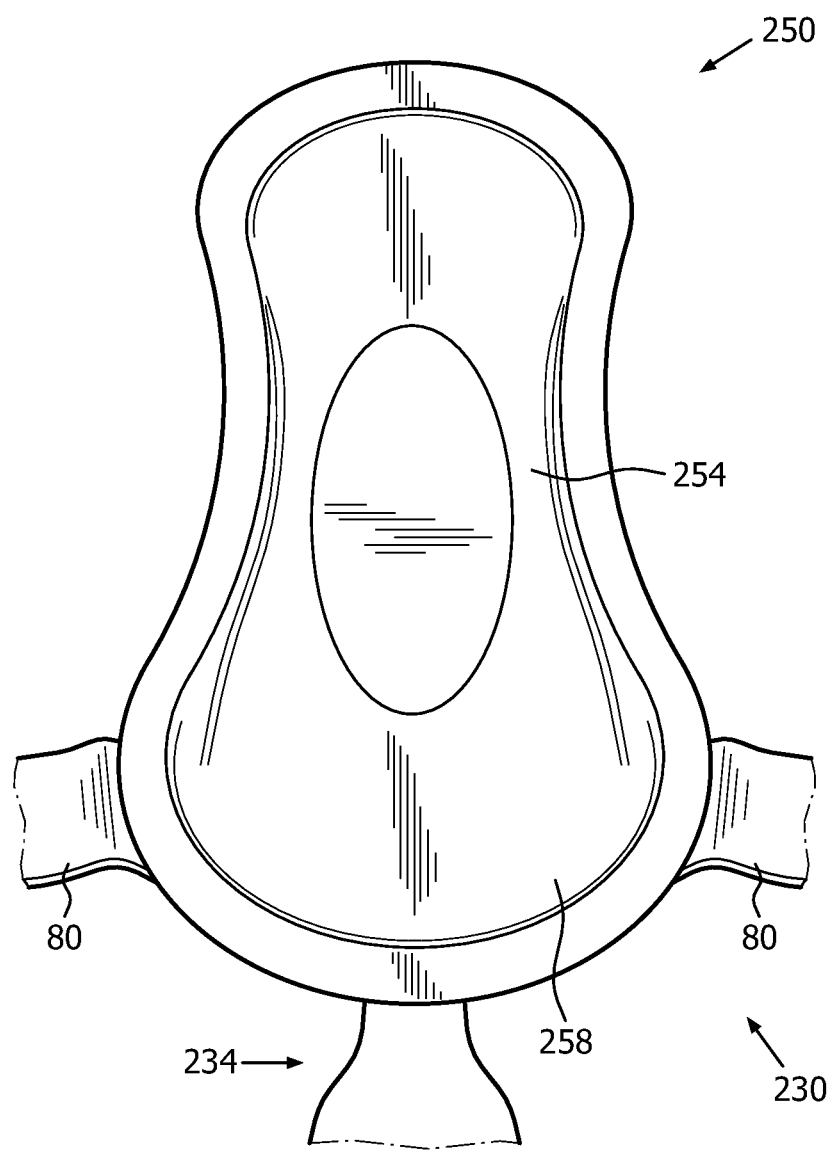
FIG. 18 is a rear view of a portion of the headgear assembly shown in FIG. 17.

An eighth embodiment of a patient interface system 230 according to the principles of the present invention shown being worn by a user is shown in FIGS. 17 and 18. Patient interface system 230, includes a patient interface assembly 232 and a headgear assembly 250. Patient interface assembly 232 includes a coupling assembly 234 that is generally similar to coupling assembly 154 discussed above with respect to and shown in FIG. 13. Coupling assembly 234 includes a forehead arm 236 that includes a headgear coupling element 238 and headgear attachment elements 240a and 240b.

Headgear assembly 250 include a pad support 252 and pad 254 coupled to the pad support. Headgear assembly also includes a coupling assembly attachment assembly 256 coupled to pad support 252. Coupling assembly attachment assembly 256 is generally similar to coupling assembly attachment assembly 176 discussed above with respect to and shown in FIG. 13. Namely, coupling assembly attachment assembly 256 is a relatively wide strap that inserts through a slot in the forehead arm and is secured back onto the headgear assembly.

Headgear assembly 250 differs from the headgear assemblies of the previous embodiments in the configuration of forehead pad 254. Notably, forehead pad 254 is sized and configured such that a lower portion 258 of the forehead pad is disposed between the user and all or part of coupling assembly 234, in particular, forehead arm 236, when the patient interface system is donned by the user. This embodiment provides a large unitary pad surface between the user and the components of the coupling assembly. It should be noted that in this embodiment, there are no forehead pads, such as forehead pad 58, disposed on forehead arm 236. If the user desires to use the patient interface assembly by itself, i.e., without headgear assembly 250, the present invention contemplates providing an attachment structure on forehead arm 236 so that a forehead pad or pads can be coupled to the forehead arm.

The present invention contemplates that the forehead arm or other portions of the coupling assembly can be secured to pad 254. For example, the hook portion of a hook-and-loop fastener can be fixed to the underside of forehead arm 236 so that the hook portion can engage the soft (loop) material on the surface of pad 254. Of course, other types of fasteners can be used to secure the forehead arm to pad 254.

Figure 19:
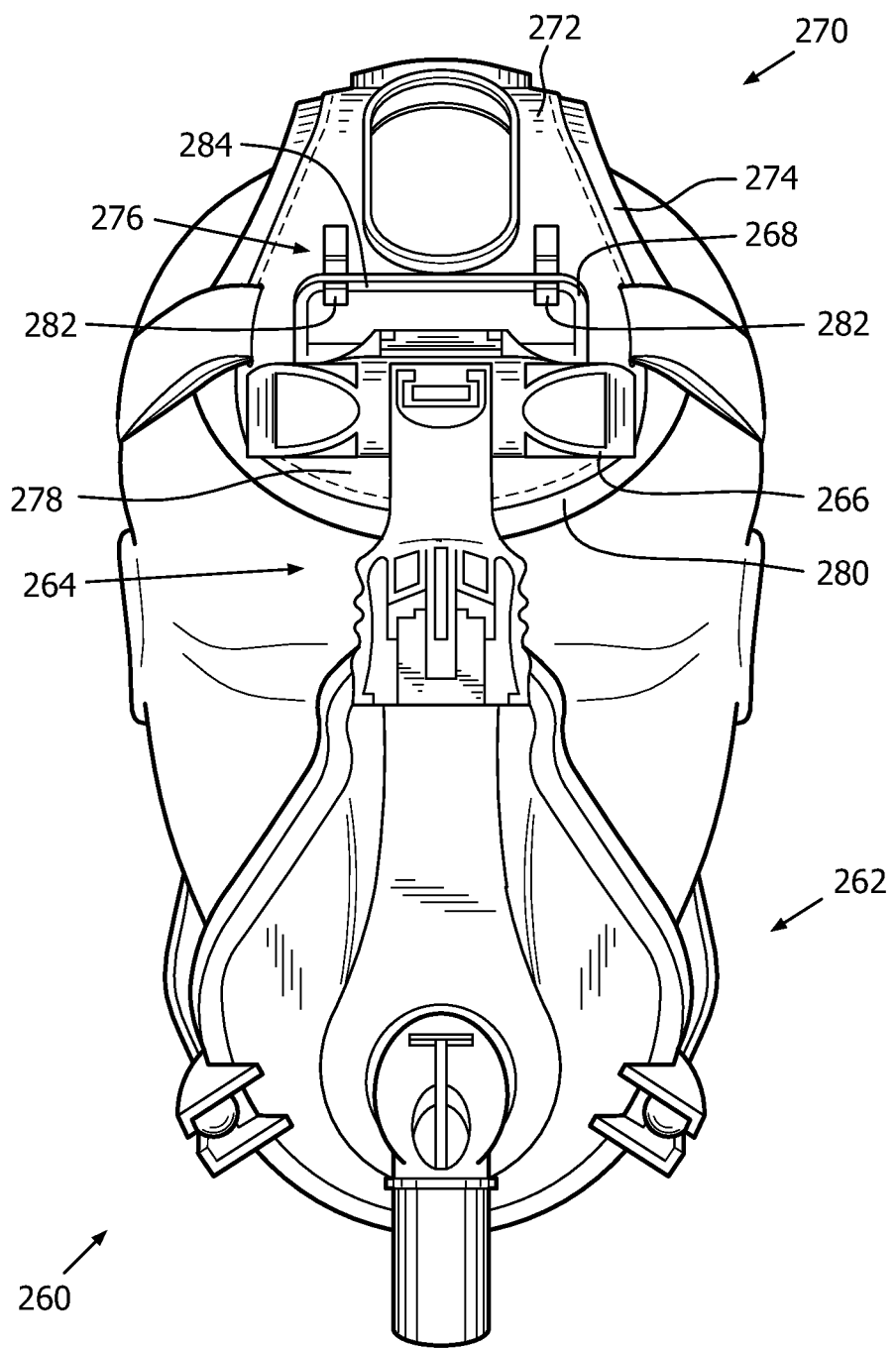
FIG. 19 is a front view of a ninth embodiment of a patient interface system according to the principles of the present invention shown being worn by a user.

FIG. 19 illustrates a ninth embodiment of a patient interface system 260 according to the principles of the present invention. Patient interface system 260 includes a patient interface assembly 262 and a headgear assembly 270. Patient interface assembly 262 includes a coupling assembly 264 that is generally similar to coupling assembly 154 discussed above with respect to and shown in FIG. 13. Coupling assembly 264 includes a forehead arm 266 that includes a headgear coupling element 268. Coupling assembly 264, and forehead arm 266 in particular, can include headgear attachment elements so that the patient interface assembly can be used without the headgear assembly.

Headgear assembly 270 includes a pad support 272 and pad 274 coupled to the pad support. Headgear assembly also includes a coupling assembly attachment assembly 276 coupled to pad support 272. In this embodiment, pad support 272 includes a lower portion 278 and pad 274 includes a lower portion 280. Both lower portions 278 and 280 are disposed between the user and all or portions of coupling assembly 264 when patient interface assembly 262 is coupled to headgear assembly 270. In the illustrated exemplary embodiment, forehead arm 266 is disposed over both the pad support and the pad of headgear assembly 270, when the headgear assembly is coupled to the forehead arm.

In this exemplary embodiment, coupling assembly attachment assembly 276 includes a pair of relatively rigid hooks 282 that are fixed to pad support 272. Hooks 282 couple to bar 284 in headgear coupling element 268 to provide a strong, yet removable connection for the patient interface assembly to the headgear assembly.

As noted above, headgear assembly 270 also includes a pair of headgear attachment elements so that headgear 80 can be attached to the pad support. The headgear attachment elements can be any suitable configuration, such as a slots, snaps, clips, etc.

Figure 20:
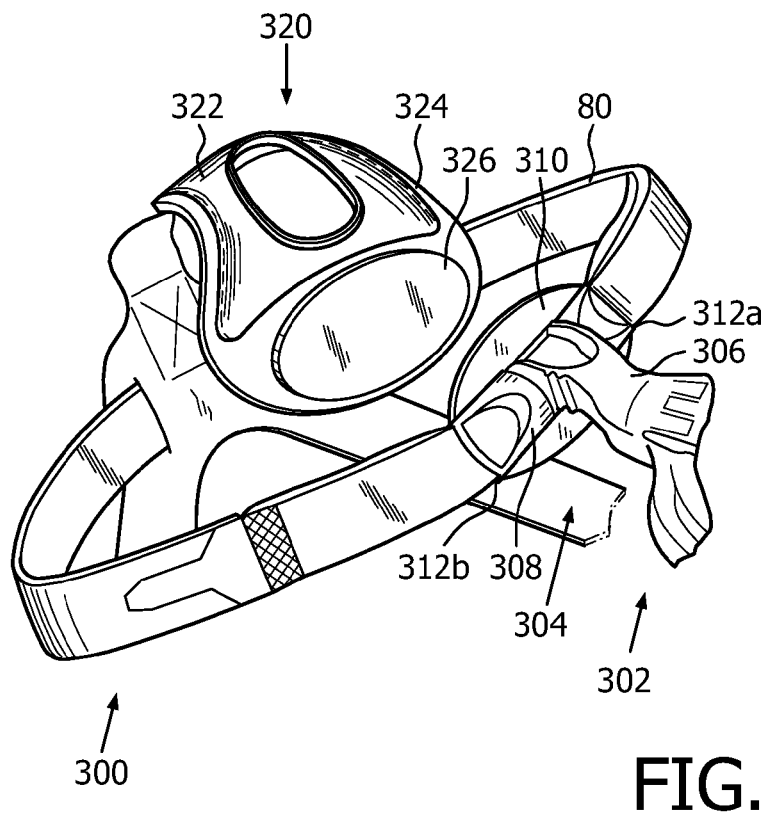
FIG. 20 is a perspective view of a portion of a patient interface system according to an tenth embodiment of the present invention.
Figure 21:
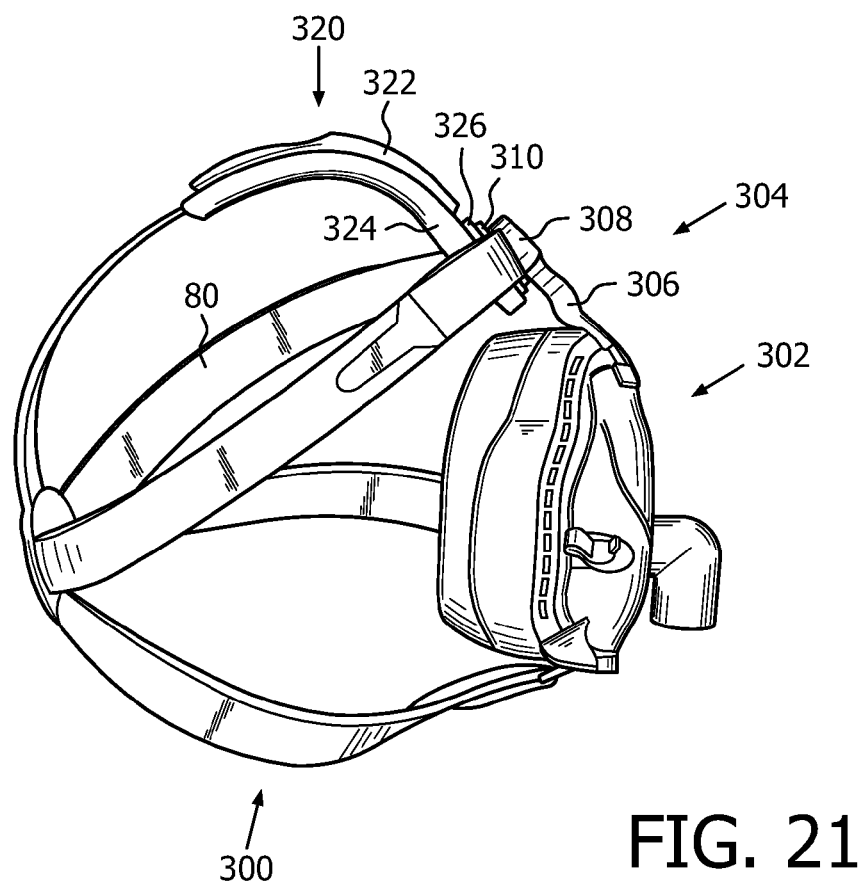
FIG. 21 is a side view of the patient interface system of FIGS. 20.

FIG. 20 illustrates an tenth embodiment of a patient interface system 300 according to the principles of the present invention. Patient interface system 300 includes a patient interface assembly 302 and a headgear assembly 310. Patient interface assembly 302 includes a coupling assembly 304 that is generally similar to coupling assembly 154 discussed above with respect to and shown in FIG. 13. Coupling assembly 304 includes a support arm 306 and a forehead arm 308. A forehead pad 310 is attached to forehead arm 306. Forehead pad 310 is also used to attach the forehead arm to the headgear assembly, as discussed in detail below. The forehead arm further includes a pair of headgear attachment elements 312a and 312b disposed at each end of the forehead arm. Although headgear attachment elements 312a and 312b can be any suitable device or technique for attaching headgear strap 80 to the forehead arm, in the illustrated embodiment, the headgear attachment elements are merely slots provided at each end of the forehead arm through which the headgear strap inserts.

Headgear assembly 320 includes a pad support 322 and pad 324 coupled to the pad support. Headgear assembly also includes a coupling assembly attachment assembly 326. In this exemplary embodiment, coupling assembly attachment assembly 326 is one part a hook-and-loop fastener, namely the hook part, disposed on a lower portion 328 of pad 326. The other part of the hook-and-loop fastener, namely the loop part, is part of headgear coupling element 310 is on the exposed surface of forehead pad 310. Thus, this embodiment allows for quick and easy attachment of the forehead arm to the headgear assembly by placing and/or pressing the forehead pad onto coupling assembly attachment assembly 326 so that the hook-and-loop fastener engages these two elements together. It can also be appreciated that this embodiment allows the patient interface assembly to be used without the headgear assembly, with forehead pad 310 serving to contact the surface of the user under the forehead arm.

Figure 22:
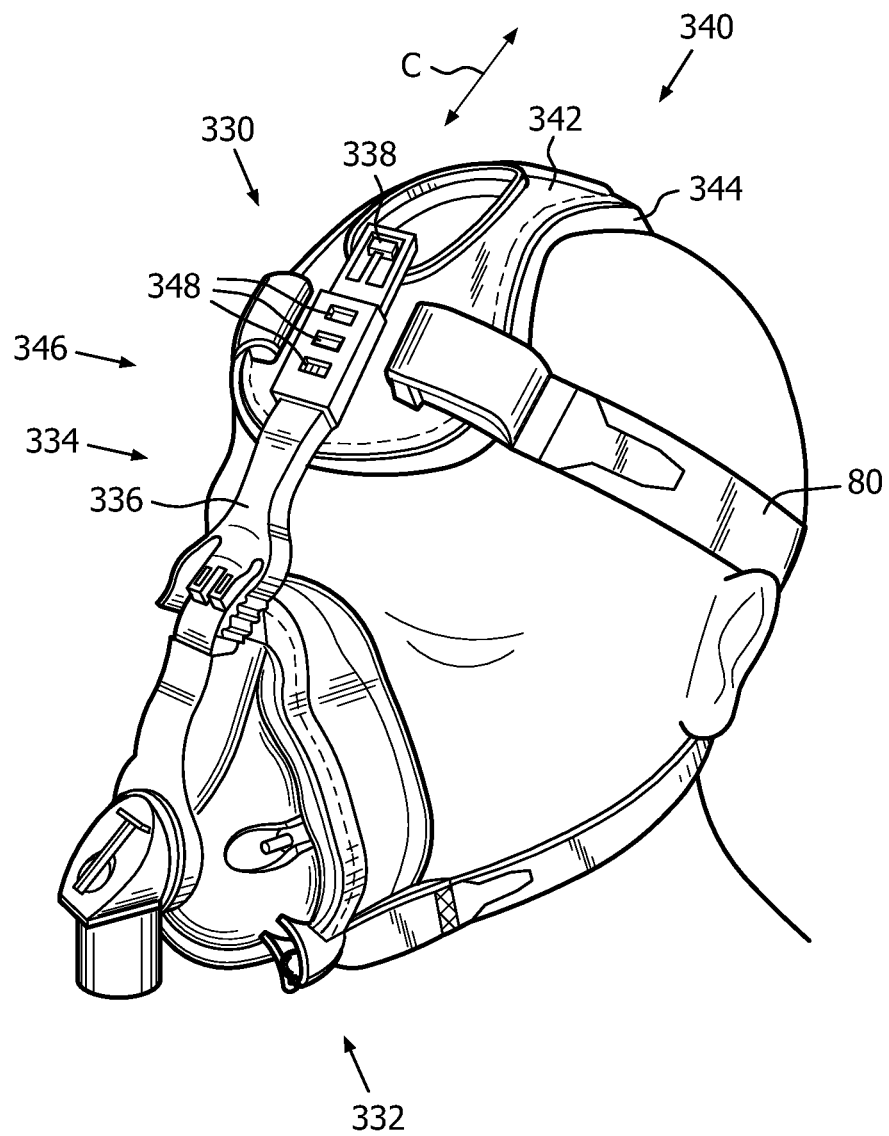
FIG. 22 is a front perspective view of eleventh embodiment of a patient interface system according to the principles of the present invention.

An eleventh embodiment of a patient interface system 330 according to the principles of the present invention is shown in FIG. 22. Patient interface system 330 includes a patient interface assembly 332 and a headgear assembly 340. Patient interface assembly 332 includes a coupling assembly 334 that includes a support arm 336. In this embodiment, there is no forehead arm as in the previous embodiments. Instead, support arm attaches directly to the headgear assembly as discussed in detail below.

Headgear assembly 340 includes a pad support 342 and pad 344 coupled to the pad support. Headgear assembly also includes a coupling assembly attachment assembly 346. Coupling assembly attachment assembly 346 defines a slot into which support arm 336 slides, as indicated by arrow C. The support arm is lockable within the slot over a plurality of discrete positions. This is accomplished by providing at least one movable locking tab 338 coupled to the support arm. In the illustrated exemplary embodiment, locking tab 338 is disposed on a cantilevered arm such that the tab can be flexed into and out of engagement with one of slots 348 provided in coupling assembly attachment assembly 346. In the illustrated embodiment, to locking tabs are provided in support arm 336 to provide a greater number of possible locking positions for the support arm relative to the headgear assembly than is possible with just one locking tab.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface system comprising:
   (a) a patient interface assembly comprising:
      (1) a frame,
      (2) a patient circuit connector disposed on a first side of the fame,
      (3) a seal member disposed on a second side of the frame opposite the first side and adapted to seal against a surface of a user, and
      (4) a coupling assembly extending from the frame, the coupling assembly being separate from and not extending from the patient circuit connector, wherein the coupling assembly is directed toward a forehead of a user responsive to the patient interface assembly being worn by such a user, the coupling assembly including a support arm, a forehead arm provided at a distal end of the support arm, and a forehead pad coupled to a bottom surface of the forehead arm; and
   (b) a headgear assembly comprising:
      (1) an elongated pad support,
      (2) a headgear attachment element (associated with the pad support,
      (3) a headgear strap coupled to the headgear attachment element,
      (4) an elongated headgear pad coupled to a bottom surface of the pad support, wherein the pad support and the headgear pad are configured so as to extend from a forehead region of a user generally along a centerline of such a user and terminate proximate to a top of a head of such a user responsive to the patient interface assembly being worn by such a user, the pad support and the headgear pad each having a cutout portion provided in an outer perimeter thereof that is sized and configured to generally match a size and shape of the forehead arm and the forehead pad, wherein the forehead arm and the forehead pad are fit and received within the headgear assembly at the cutout portion of the pad support and the headgear pad responsive to the patient interface assembly being assembled with the headgear assembly in manner wherein an outer edge of the forehead pad is adjacent to and in an abutting relationship with an outer edge of the headgear pad, and wherein the headgear pad and the forehead pad have a uniform height, and
      (5) a coupling assembly attachment assembly operatively coupled to the pad support and adapted to couple the coupling assembly of the patient interface device to the headgear assembly.

2. The patient interface assembly of claim 1, wherein the frame defines a nose receiving cavity.

3. The patient interface assembly of claim 1, wherein the seal member is sized and configured to enclose a mouth and nares of a user responsive to the patient interface assembly being worn by such a user.

4. The patient interface assembly of claim 1, wherein the patient circuit connector is a rotatable elbow coupling.

5. The patient interface assembly of claim 1, wherein the coupling assembly is adjustably coupled to (a) the frame, (b) the coupling assembly attachment assembly, or (c) both (a) and (b).

6. The patient interface assembly of claim 1, wherein the coupling assembly comprises:
   a headgear coupling element coupled to the forehead arm and adapted to selectively couple to the coupling assembly attachment assembly of the headgear assembly.

7. The patient interface assembly of claim 6, wherein (a) the headgear coupling element is a slot and the coupling assembly attachment assembly includes a member adapted to be inserted into the slot, or (b) the coupling assembly attachment assembly is a slot and the headgear coupling element includes a member adapted to be inserted into the slot.

8. The patient interface assembly of claim 6, further comprising a second headgear attachment element coupled to the forehead arm.

9. The patient interface assembly of claim 6, wherein the coupling assembly is configured to be moveable relative to the coupling assembly attachment assembly between a first position and a second position responsive to the patient interface assembly being assembled with the headgear assembly, and wherein in the first position the coupling assembly cannot be disengaged from the headgear assembly and in the second position the coupling assembly can be freely disengaged from the headgear assembly.

10. A patient interface system comprising:
(a) a patient interface assembly comprising:
  (1) a frame,
  (2) a patient circuit connector disposed on a first side of the fame, and
  (3) sealing means, operatively coupled to a second side of the frame opposite the first side, for sealing against a surface of a user;
(b) a headgear assembly comprising:
  (1) an elongated pad support,
  (2) a headgear strap,
  (3) a headgear means for coupling the headgear strap to the pad support, and
  (4) an elongated headgear pad coupled to a bottom surface of the pad support, wherein the pad support and the headgear pad are configured so as to extend from a forehead region of a user generally along a centerline of such a user and terminate proximate to a top of a head of such a user responsive to the patient interface assembly being worn by such a user; and
(c) coupling means for coupling the headgear assembly to the patient interface assembly, the coupling means being separate from and not extending from the patient circuit connector the coupling means including a support arm, a forehead arm provided at a distal end of the support arm and a forehead pad coupled to a bottom surface of the forehead arm, wherein the pad support and the headgear pad each have a cutout portion provided in an outer perimeter thereof that is sized and configured to generally match a size and shape of the forehead arm and the forehead pad, wherein the forehead arm and the forehead pad are fit and received within the headgear assembly at the cutout portion of the pad support and the headgear pad responsive to the patient interface assembly being assembled with the headgear assembly in manner wherein an outer edge of the forehead pad is adjacent to and in an abutting relationship with an outer edge of the headgear pad, and wherein the headgear pad and the forehead pad have a uniform height.

11. The system of claim 10, wherein the coupling means provides an adjustable coupling between the pad support and the frame.

12. The system of claim 10, wherein the coupling means further comprises:
  second coupling means for adjustably coupling the second end portion of the support arm to the headgear assembly.

\* \* \* \* \*